US011377692B2

(12) United States Patent
Tanackovic Abbas-Terki et al.

(10) Patent No.: US 11,377,692 B2
(45) Date of Patent: *Jul. 5, 2022

(54) METHOD FOR PREDICTING THE RISK OF DEEP VEIN THROMBOSIS AND PULMONARY EMBOLISM ASSOCIATED WITH HORMONAL PREPARATIONS AND HORMONE LEVELS

(71) Applicant: GENE GENDER S.R.L., Milan (IT)

(72) Inventors: Goranka Tanackovic Abbas-Terki, Lausanne (CH); Joëlle Michaud Schutz, Lausanne (CH); Thierry Daniel Pache, Lausanne (CH)

(73) Assignee: GENE GENDER S.R.L., Milan (IT)

( * ) Notice: Subject to any disclaimer, the term of this patent is extended or adjusted under 35 U.S.C. 154(b) by 165 days.

This patent is subject to a terminal disclaimer.

(21) Appl. No.: 16/468,074

(22) PCT Filed: Dec. 11, 2017

(86) PCT No.: PCT/EP2017/082164
§ 371 (c)(1),
(2) Date: Jun. 10, 2019

(87) PCT Pub. No.: WO2018/104549
PCT Pub. Date: Jun. 14, 2018

(65) Prior Publication Data
US 2020/0071762 A1 Mar. 5, 2020

(30) Foreign Application Priority Data

Dec. 9, 2016 (EP) .................................... 16203286
Mar. 30, 2017 (EP) .................................... 17163897

(51) Int. Cl.
*C12Q 1/68* (2018.01)
*C12Q 1/6883* (2018.01)

(52) U.S. Cl.
CPC ..... *C12Q 1/6883* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,910,303 B2 * | 3/2011 | Bare | A61P 7/02 435/6.11 |
| 2009/0270332 A1 * | 10/2009 | Bare | G01N 35/00 514/56 |
| 2010/0227776 A1 * | 9/2010 | Wu | C12Q 1/6886 506/13 |

FOREIGN PATENT DOCUMENTS

| | | | |
|---|---|---|---|
| EP | 2 535 424 A1 | 12/2012 | |
| EP | 2535424 A1 * | 12/2012 | ........... C12Q 1/6827 |
| WO | 2015/091115 A1 | 6/2015 | |

OTHER PUBLICATIONS

Bruzelius et al. Predicting venous thrombosis in women using a combination of genetic markers and clinical risk factors. Thromb Haemost; 2015; 13;2;219-227. (Year: 2015).*
Bruzelius et al. Predicting venous thrombosis in women using a combination of genetic markers and clinical risk factors. Journal of Thrombosis and Haemostasis; 2014; 13: 219-227. (Year: 2014).*
Li et al. Association of genetic loci for migraine susceptibility in the she people of China. The Journal of Headache and Pain; 2015; 16; 70: 1-7. (Year: 2015).*
Blanco-Molina et al. Progestin-only contraception and venous thromboembolism. Thrombosis Research; 2012; 129; 5: e257-e262. (Year: 2012).*
Saccp and Ripa. Migraine in pregnancy. The Journal of Headache and Pain 2015, 16(Suppl 1):A24. (Year: 2015).*
Winsvold et al. Genetic analysis for a shared biological basis between migraine and coronary artery disease. Neurol Genet 2015; 1: e10:p. 1-12. (Year: 2015).*
Bruzelius et al. Journal of Thrombosis and Haemostasis; 2014; 13: 219-227. (Year: 2014).*
Sacco and Ripa. The Journal of Headache and Pain 2015, 16(Suppl 1):A24. (Year: 2015).*
Winsvold et al. Neurol Genet 2015; 1: e10: p. 1-12. (Year: 2015).*
Bruzelius et al. Journal of Thrombosis and Haemostasis; 2014; 13: 219-227, cited in IDS. (Year: 2014).*
Blanco-Molina et al. Thrombosis Research; 2012; 129; 5: e257-e262. (Year: 2012).*
Lin et al. The Journal of Headache and Pain; 2015; 16; 70: 1-7. (Year: 2015).*
Dahm et al. British Journal of Haematology; 2012; 157: 753-761. (Year: 2012).*
De Haan et al., "Multiple SNP testing improves risk prediction of first venous thrombosis," Blood, Jul. 19, 2012, vol. 120, No. 3, pp. 656-663.
Bruzelius et al., "Predicting venous thrombosis in women using a combination of genetic markers and clinical risk factors," Journal of Thrombosis and Haemostatis, 2014, vol. 13, pp. 219-227.
Morange et al., "Genetics of Venous Thrombosis: update in 2015," Thrombosis and Haemostasis, 2015, vol. 114, No. 5, pp. 910-919.
May 3, 2018 International Search Report issued in International Patent Application No. PCT/EP2017/082164.

* cited by examiner

*Primary Examiner* — Juliet C Switzer
*Assistant Examiner* — Wahwah T Johnson
(74) *Attorney, Agent, or Firm* — Oliff PLC

(57) ABSTRACT

Specific single nucleotide polymorphisms (SNPs) in the human genome, and their association with deep vein thrombosis (DVT) and related pathologies, such as pulmonary embolism (PE), in relation with hormonal preparations (i.e. combined contraceptives, hormone replacement therapeutics) and hormone levels (i.e. during pregnancy and postpartum).

6 Claims, 3 Drawing Sheets
Specification includes a Sequence Listing.

FIG: 1
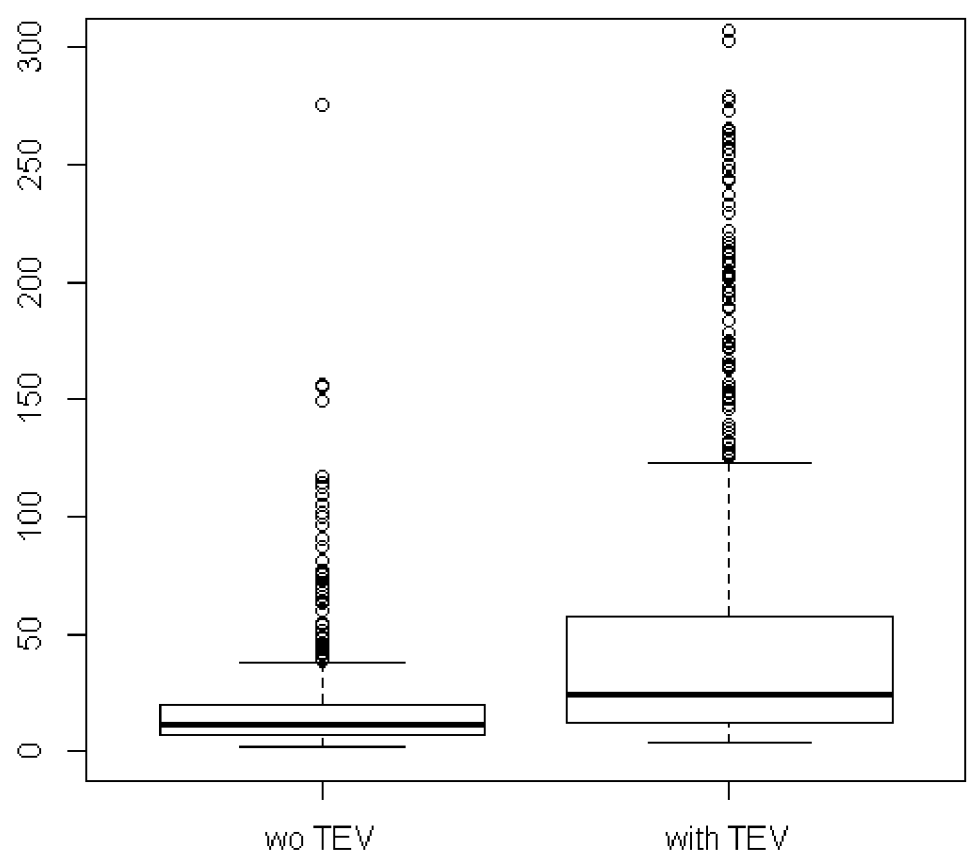

FIG: 2
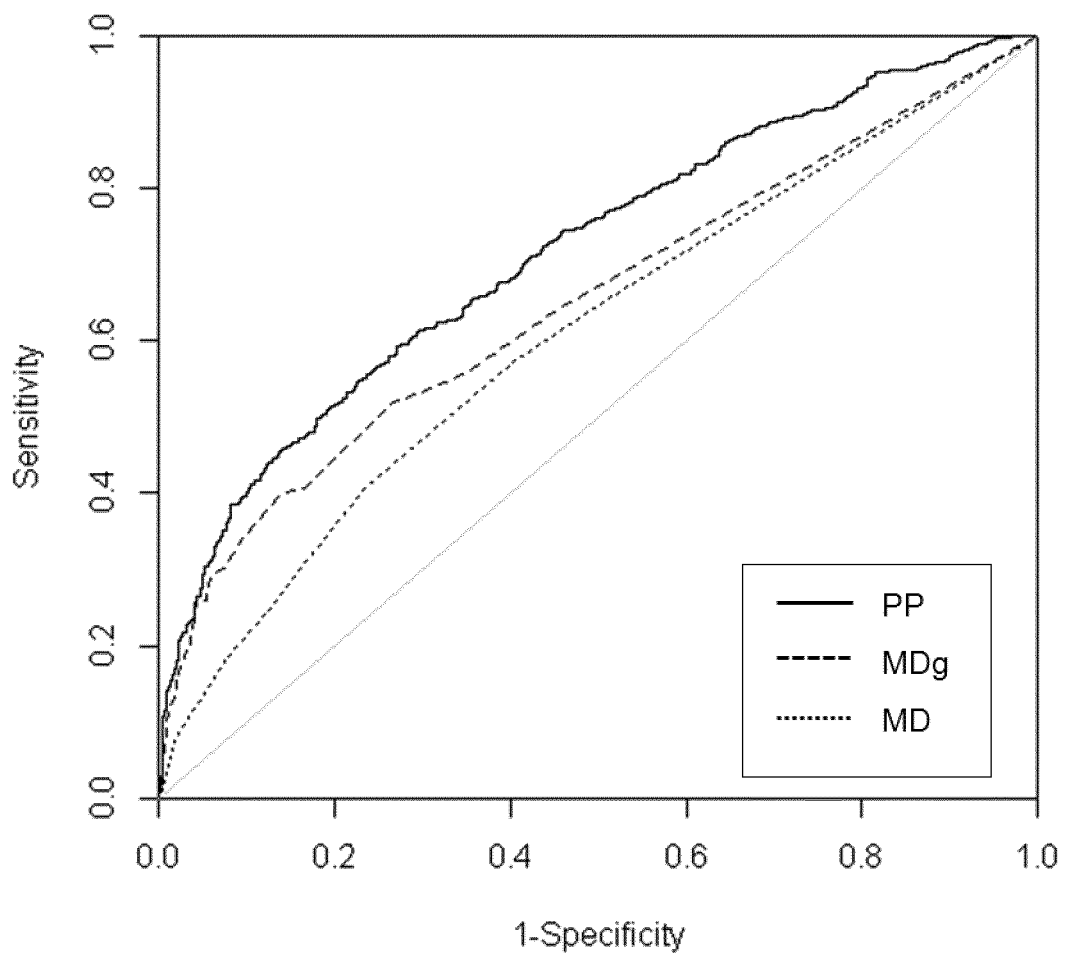

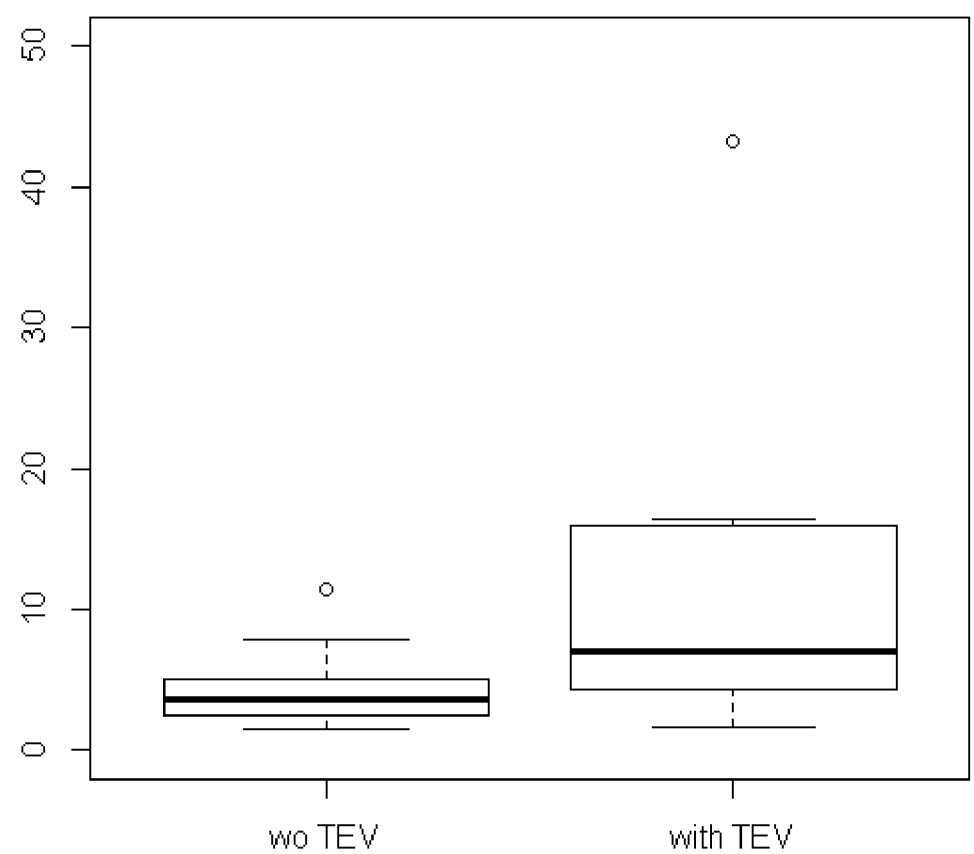
FIG: 3

METHOD FOR PREDICTING THE RISK OF DEEP VEIN THROMBOSIS AND PULMONARY EMBOLISM ASSOCIATED WITH HORMONAL PREPARATIONS AND HORMONE LEVELS

The present application contains a Sequence Listing that has been submitted electronically in ASCII format and is hereby incorporated by reference in its entirety. The ASCII copy, created on Feb. 22, 2022, is named Substitute Sequence Listing_ST25.txt and is 3,275 bytes in size.

TECHNICAL FIELD

The invention relates to the field of medicine, in particular to the field of blood clotting diseases prognosis. Specifically, the present invention relates to specific single nucleotide polymorphisms (SNPs) in the human genome, and their association with deep vein thrombosis (DVT) and related pathologies, such as pulmonary embolism (PE), in relation with hormonal preparations (e.g. combined contraceptives, or hormone replacement therapies) and hormone levels (e.g. during pregnancy, or post-partum).

BACKGROUND OF THE INVENTION

Venous thrombosis is a serious medical condition that occurs when a blood clot (thrombus) forms in one or more veins of the body. One particular form of venous thrombosis is called deep vein thrombosis when the blood clot occurs in deep veins. Such blood clots might travel through the bloodstream and lodge in lungs, where they can block blood flow, causing pulmonary embolism. Several inherited or acquired conditions can increase coagulability of blood and thus the tendency to develop blood clots. The inherited conditions include mutations in the diverse well-known clotting, anticoagulant, or thrombolytic factors, such as the.factor V Leiden mutation (in the.factor V gene), mutations in the prothrombin gene (factor 11), or in the methylenetetrahydrofolate reductase gene (MTHFR). Additional mutations can be present in genes coding for protein C and protein S although they are rare. Other likely inherited causes include a possible increase in the expression of procoagulant factors such as factor VIII, von Willebrand factor, and factors IX and XI (Cushman M, (2005). Hematology Am Soc Hematol Educ Program: 452-457). Examples of the acquired conditions that can cause DVT are surgery and trauma, prolonged immobilization, cancer, myeloproliferative disorders, and even pregnancy and post-partum (Seligsohn U. and Lubetsky A., (2001) New Eng J Med 344(16): 1222-1231). DVT might occur as the result of a genetic mutation alone or in concert with behavioural and environmental factors, such as prolonged immobilisation, smoking and hormonal treatments. Thus, DVT is considered complex or multifactorial disease.

Over 100 million women worldwide use combined estroprogestative contraceptives (CC), due to their very high effectiveness in reducing the risk of unwanted pregnancy and their beneficial effect on diverse symptoms related to women's cycle. Nonetheless, these contraceptives also increase the risk of blood clotting substantially, which can ultimately lead to DVT and PE (Vinogradova Y., Coupland C. and Hippisley-Cox J., (2015) BMJ 350: h2135). Newer generations of the CC, the so-called 3rd and 4th generation CC, are usually better tolerated by women but importantly they increase the risk of developing DVT even more than the older preparations of the so-called $2^{th}$ and $1^{st}$ generations.

The incidence of thrombosis among CC users is around 1‰, which is 10 times more than in population in general of the same age. In France alone, where over 3 M women aged 15-49 use CC, the National Agency for the Safety of Drugs and Health Products reports every year over 2'500 cases of DVT, 850 cases of PE, and 20 cases of death linked to contraceptive pills. According to recent estimates, in Europe, 22'000 DVT cases related to CC occur each year. Thus, one of the major challenges for healthcare professionals is to identify women at risk of developing DVT related to CC, and advise them on alternative contraception methods.

As the standard of care nowadays, prescribing physicians use a medical questionnaire to assess the risk of thrombosis, mostly focusing on age, body mass index and smoking habits that are known risk factors for disease development, as well as on the personal and familial history of DVT or related diseases. If the familial or personal history is positive, physicians test for the thrombophilic status of the patient (complete or partial blood analysis including two genetic risk factors: the factor V-Leiden and the prothrombin mutations). Taking into account the currently registered number of thrombosis cases related to CC, this approach is a relatively low performing one, with suboptimal sensitivity and specificity. This observation is further confirmed through diverse studies that demonstrate that these information, notably familial history, are insufficient to reliably estimate risk of DVT (de Haan H. G. et al., (2012). Blood 120: 656-663; Suchan P, et al., (2015). Thrombosis and Haemostasis 114(6)).

Different studies have tried to combine further genetic and clinical parameters to predict individuals at risk of thrombosis (de Haan H. G. et al., (2012) Blood 120: 656-663, Bruzelius, et al., (2015) J. Thromb Haemost. 13(2):219-27). Nonetheless, these approaches were not focused at women undergoing hormonal changes, but included all kind of patients that developed thrombosis (e.g. cancer patients, patients undergoing immobilisation, surgery, etc). Thus, the impact of these models in predicting risk of thrombosis for women undergoing hormonal changes remained unclear until now.

Hormone replacement therapy for menopause (HRT) aims to prevent discomfort caused by diminished circulating estrogen and progesterone hormones in woman's body, or in the case of the surgically or prematurely menopaused women, it aims at prolonging life and reducing the occurrence of osteoporosis and dementia. It involves use of preparations that usually include estrogens and progesterone or progestins. As in the case of contraceptive treatments, these hormones and consequently the replacement treatments increase importantly the risk of developing DVT and PE. It is now well established that the presence of the factor V Leiden mutation and prothrombin mutation has a multiplicative effect on the overall risk of DVT related to hormone replacement therapy (Douketis J. D. et al., (2011). Clin Appl Thromb Hemost. 17(6): E106-113; Botto N., et al., (2011). Climacteric. 14(1): 25-30). Nonetheless, there are no precise methods available to estimate the risk of DVT related to HRT use.

Thus, considering women subjects undergoing a change in hormone levels, there remains significant unmet need to develop a prognostic method for identifying if a woman is at risk of developing a blood clotting disease and to develop a method for calculating such risk with improved sensitivity and specificity.

SUMMARY or THE INVENTION

The present invention provides a prognostic method for identifying if a woman subject undergoing a change in hormone levels is at risk of developing a blood clotting disease, the method comprising the steps of:
a) Determining in a sample from said woman subject the genotype of single nucleotide polymorphism of rs1 799853 (SEQ ID NO:1), rs4379368 (SEQ ID NO:2), rs6025 (SEQ ID NO:3), rs1 799963 (SEQ ID NO:4), rsS1 76719 (SEQ ID NO:5), rsS1 76750 (SEQ ID NO:6), rs9574 (SEQ ID NO:7), rs2289252 (SEQ ID NO:8), and rs710446 (SEQ ID NO:9):
b) Determining the clinical risk factors of said woman subject, said clinical risk factors are selected from the group comprising the smoking status, the BMI, the age, the familial history of blood clotting diseases and the change in hormone levels:
c) Combining the genotyping data of step a) and the clinical risk factors of step b) on a decision support algorithm that gives a risk score; and
d) Analysing the risk score in order to determine the risk of said woman subject to develop a blood clotting disease.

The invention also provides an apparatus for calculating an estimation value of the risk of developing a blood clotting disease in a woman subject undergoing a change in hormone levels based on the woman subject-specific input features, said apparatus comprising:
a) a data interface for receiving said input features;
b) a processor for calculating said estimation value by applying a decision support algorithm as a function of numerical values derived from said received input features; and
c) a user interface for outputting said estimation value:
wherein said input features include a combination of:
  (i) the genotype of single nucleotide polymorphism of rs1799853 (SEQ ID NO:1), 1 rs4379368 (SEQ ID NO:2), rs6025 (SEQ ID NO:3), rs1 799963 (SEQ ID NO:4), rs8176719 (SEQ ID NO:5), rs8176750 (SEQ ID NO:6), rs9574 (SEQ ID NO:7), rs2289252 (SEQ ID NO:8), and rs710446 (SEQ ID NO:9); and
  (ii) the clinical risk factors comprising the smoking status, the BMI, the age, the familial history of blood clotting diseases and the change in hormone levels of said woman subject.

Also provided is a method for calculating an estimation value of the risk of developing a blood clotting disease in a woman subject undergoing a change in hormone levels based on woman subject-specific input features, said method comprising:
a) selecting said input features to include a combination of:
  (i) the genotype of single nucleotide polymorphism of rs1799853 (SEQ ID NO:1), rs4379368 (SEQ ID NO:21, rs6025 (SEQ ID NO:3), rs1 799963 (SEQ ID NO:4), rs8176719 (SEQ ID NO:5), rs8176750 (SEQ ID NO:6), rs9574 (SEQ ID NO:7), rs2289252 (SEQ ID NO:8), and rs710446 (SEQ ID NO:9); and
  (ii) the clinical risk factors comprising the smoking status, the BMI, the age, the familial history of blood clotting diseases and the change in hormone levels of said woman patient; and
b) calculating said estimation value by applying a decision support algorithm as a function of numerical values derived from said received input features.

The invention further provides a kit for use in identifying if a woman subject undergoing a change in hormone levels is having a risk of developing a blood clotting disease, said kit comprising
i) at least one detection reagent for detecting the genotype of single nucleotide polymorphism of rs1 799853 (SEQ ID NO:1), rs4379368 (SEQ ID NO:2), rs6025 (SEQ ID NO:3), rs1 799963 (SEQ ID NO:4), rs8176719 (SEQ ID NO:5), rs8176750 (SEQ ID NO:6), rs9574 (SEQ ID NO:7), rs2289252 (SEQ ID NO:8), and rs710446 (SEQ ID NO:9);
and optionally
ii) instructions for use.

BRIEF DESCRIPTION OF THE FIGURES

FIG. 1: Pill Protect® (PP) risk score distribution for 1622 women on hormonal contraceptives. woTEV=controls, women who have not developed thrombosis. With TEV=cases, women who have developed thrombosis.

FIG. 2: ROC curves for PP (full line), MD (dotted line) and MDg (straight dashed line) scores among the 1622 women on hormonal contraceptives.

FIG. 3: Pill Protect® (PP) score distribution for 26 women eligible for HRT. woTEV=controls women who have not developed thrombosis. With TEV=subjects who have developed thrombosis.

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control.

Unless defined otherwise, all technical and scientific terms used herein have the same meaning as is commonly understood by one of skill in art to which the subject matter herein belongs. As used herein, the following definitions are supplied in order to facilitate the understanding of the present invention.

Other objects and advantages of the invention will become apparent to those skilled in the art from a review of the ensuing detailed description, which proceeds with reference to the following illustrative drawings, and the attendant claims.

The term "comprise" is generally used in the sense of include, that is to say permitting the presence of one or more features or components.

As used in the specification and claims, the singular forms "a", "an" and "the" include plural references unless the context clearly dictates otherwise.

As used herein the terms "subject" or "patient" are well-recognized in the art, and, are used interchangeably herein to refer to a "woman undergoing a change in hormone levels", in particular female hormone levels, either induced by a treatment (for example contraceptives and/or hormone replacement therapy) or naturally occurring (for example pregnancy and postpartum). In some embodiments, the subject is a subject in need of treatment or a subject with a disease or disorder. However, in other embodiments, the subject can be a normal woman subject. The term does not denote a particular age.

The present invention relates to the identification of novel single nucleotide polymorphisms (SNPs) and unique combinations of such SNPs, as well as combination of SNPs and clinical risk factors (behavioural and environmental factors) that are associated with risk of developing blood clotting diseases such as deep vein thrombosis (DVT) and Pulmonary embolism (PE) for women subjects undergoing a change in hormone levels.

The present invention provides a prognostic method for identifying if a woman subject undergoing a change in hormone levels is at risk of developing a blood clotting disease, the method comprising the steps of:

a) Determining in a sample from said woman subject the genotype of single nucleotide polymorphism of rs1799853 (SEQ ID NO:1), rs4379368 (SEQ ID NO:2), rs6025 (SEQ ID NO:3), rs1799963 (SEQ ID NO:4), rs8176719 (SEQ ID NO:5), rs8176750 (SEQ ID NO:6), rs9574 (SEQ ID NO:7), rs2289252 (SEQ ID NO:8), and rs710446 (SEQ ID NO:9):

b) Determining the clinical risk factors of said woman subject, said clinical risk factors are selected from the group comprising the smoking status, the BMI, the age, the familial history of blood clotting diseases and the change in hormone levels;

c) Combining the genotyping data of step a) and the clinical risk factors of step b) on a decision support algorithm that gives a risk score; and d) Analysing the risk score in order to determine the risk of said woman subject to develop a blood clotting disease.

As used herein, the term "blood clotting disease" refers to diseases selected from the group comprising vein thrombosis, deep vein thrombosis (DVT), pulmonary embolism (PE) and arterial thrombosis.

Preferably, the present invention provides a prognostic method for identifying if a woman subject undergoing a change in hormone levels is at risk of developing a deep vein thrombosis and/or a pulmonary embolism.

As used herein the term "change in hormone levels" refers to any treatment that involves hormone and/or particular change in a woman's life that modifies hormone levels. In particular, treatments include combined contraceptives, progestin-only contraceptives, hormone replacement therapy, assisted reproductive technology, pregnancy and postpartum periods.

"Combined contraceptive" refers to any contraceptives that contain an estrogen combined with a progestin.

Diverse forms of variations in a DNA sequence exist. Single nucleotide polymorphisms (SNPs) are the most common ones, representing more than 90% of all differences among individuals. Precisely, a SNP is a commonly occurring DNA variation (e.g. with frequency higher than 1%) in which two chromosomes differ in a given segment a single position (a single base pair). Though SNPs are naturally and commonly occurring variations in human DNA, if they are part of the coding or regulatory DNA sequences, they might actually alter the expression of genes or stability of its transcripts and thus confer some advantages and risk to the carriers. It is now well established that these common genetic variants or their combination might be associated to some major traits, such as diseases.

The prognostic method according to the invention comprises the steps of determining in a sample from a woman subject undergoing a change in hormone levels the genotype of at least one single nucleotide polymorphism (SNP) selected from the group comprising:

TABLE 1

| rs6120849 | rs2289252 | rs9380643 |
| rs1039084 | rs11210892 | rs1801131 |
| rs2036914 | rs169713 | rs169715 |
| rs7082872 | rs5742904 | rs670659 |
| rs2288904 | rs1801133 | rs3136516 |
| rs1800790 | rs4680 | rs5985 |
| rs4981021 | rs1063856 | rs1613662 |
| rs8176747 | rs867186 | rs9574 |
| rs4524 | rs6025 | rs13146272 |
| rs7412 | rs1799963 | rs10133762 |
| rs1593812 | rs710446 | rs1799889 |
| rs1884841 | rs2227589 | rs9390459 |
| rs429358 | rs8176719 | rs1799853 |
| rs3813948 | rs1053878 | rs4379368 |
| rs8176750 | rs2228220 | |
| rs2066865 | rs5918 | |
| rs10029715 | rs1800595 | |

Further SNPs can be determined based on the SNPs described in the present invention by statistical correlation. "Linkage disequilibrium" (LD) refers to the statistical correlation between two neighboring SNPs. LD is generally quantified with either Lewontin's parameter of association (Lewontin, R. C. (1964). Genetics. 49 (1): 49-67) or with the r2 parameter based on Pearson correlation coefficient (Karl Pearson (1895) Proceedings of the Royal Society of London, 58: 240-242). When the LD value is equal to 1, the two SNPs are in complete disequilibrium. In contrast, two SNP, with a LI) value equal to o are in complete linkage equilibrium. Linkage disequilibrium is calculated following the application of the expectation maximization algorithm (EM) for the estimation of haplotype frequencies.

Thus, in the present invention. SNPs considered in LI) with rs1 799853 (SEQ ID NO: 1), rs4379368 (SEQ ID NO: 2), rs6025 (SEQ ID NO: 3), rs1 799963 (SEQ ID NO: 4), rs8176719 (SEQ ID NO: 5), rs8176750 (SEQ ID NO: 6), rs9574 (SEQ ID NO: 7), rs2289252 (SEQ ID NO: 8), or rs710446 (SEQ ID NO: 9) are SNPs with a r2 greater than 0.5.

Preferably, the prognostic method according to the invention comprises the step of determining in a sample from a woman subject undergoing a change in hormone levels the genotype of single nucleotide polymorphism of rs6025 (SEQ ID NO:3); rs1 799963 (SEQ ID NO:4); rs8176719 (SEQ ID NO:5); rs8176750 (SEQ ID NO:6); rs9574 (SEQ ID NO:7); rs2289252 (SEQ ID NO:8); rs710446 (SEQ ID NO:9); rs4379368 (SEQ ID NO:2); rs1 799853 (SEQ ID NO:1).

TABLE 2

| SEQ ID NO: | rs | Sequence | Gene |
| --- | --- | --- | --- |
| SEQ ID NO: 1 | rs1799853 | GATGGGGAAGAGGAGCA TTGAGGAC[C/T]GTGTTCA AGAGGAAGCCCGCTGCCT | CYP2C9 gene (NG_008385) |
| SEQ ID NO: 2 | rs4379368 | TGGATGGTATTGACTTTTA CATCAC[C/T]GAAGGTGTT TCCATAGATGGAAGAC | SUGCT gene (NG_023422) |

TABLE 2-continued

| SEQ ID NO: | rs | Sequence | Gene |
|---|---|---|---|
| SEQ ID NO: 3 | rs6025 | TGTAAGAGCAGATCCCTG GACAGGC[A/G]AGGAATA CAGGTATTTTGTCCTTGA | Factor V gene (NG_011806) |
| SEQ ID NO: 4 | rs1799963 | GTTCCCAATAAAAGTGAC TCTCAGY[A/G]AGCCTCAA TGCTCCCAGTGCTATTC | Factor II gene (NG_008953) |
| SEQ ID NO: 5 | rs8176719 | GCAGTAGGAAGGATGTCC TCGTGGT[-/G]ACCCCTTG GCTGGCTCCCATTGTCT | ABO gene (NG_006669) |
| SEQ ID NO: 6 | rs8176750 | CCAAGAACCACCAGGCGG TCCGGAA[-/C]CCGTGAGC GGCTGCCAGGGGCTCTG | ABO gene (NG_006669) |
| SEQ ID NO: 7 | rs9574 | GCGATGTTAATTACTCTCC AGCCCC[C/G]TCAGAAGG GGCTGGATTGATGGAGG | PROCR gene (NG_032899) |
| SEQ ID NO: 8 | rs2289252 | GTGAGGGTGAGGCTTGTC TCTCT[C/T]GCCCTCTCA TCCTGGCACATGTGCG | Factor 11 gene (NG_008051) |
| SEQ ID NO: 9 | rs710446 | AGGGATCCAATCGTCATC ACTCTGT[A/G]TGGGAGCT GGTGATATAGGAGGCAT | KNG1 gene (NG_016009) |

The prognostic method according to the invention also comprises the step of determining the clinical risk factors of said woman subject, said clinical risk factors are selected from the group comprising the smoking status, the BMI, the age, the familial history of blood clotting diseases, the change in hormone levels, the personal history of blood clotting diseases (such as DVT and/or PE), the alcohol status, a personal history of hypertension, of cholesterol, of diabetes, of autoimmune disease, of cancer and of other cardiovascular diseases, the history of contraception, the duration of the contraception, and the concomitant use of other drugs.

Preferably, the clinical risk factors are selected from the group consisting of the smoking status, the BMI, the age, the familial history of blood clotting diseases and/or the change in hormone levels.

A value (variable xn) is assigned for each clinical factors and is used to calculate the score Pill Protect® (PP). Values of variables Xn are as follows:

Smoking status factor: a value of 0 is accorded to a non-smoking status, a value of 1 is accorded to a smoking status.

BMI (Body Mass Index) factor: the value corresponds to the BMI of the subject, calculated according to the weight and the height of the subject.

Age factor: the value corresponds to the age of the subject.

Familial history factor of DVT and/or PE: a value of 0 is accorded in absence of blood clotting diseases in the familial history, and a value of 1 is accorded in presence of blood clotting diseases in the familial history.

Change in hormone level: the value is dependent on the cause of change in hormone level. For example, the type of progestin included in the combined contraceptive is taken into account.

Clinical risk factors as disclosed herein may be determined through the request form sent by the physician or healthcare provider.

In the prognostic method according to the invention, the genotype of SNP is determined for example by nucleic acid sequencing and/or by PCR analysis in a sample of the woman subject undergoing a change in hormone levels.

The sample may be any biological sample, containing DNA and derived from the subject. This includes body fluids, tissues, cells, biopsies and so on. The preferred samples are saliva and blood.

The sample is collected according to the transfer method of choice and is treated to purify nucleic acids. These treatments include lysis, centrifugation and washing steps. The lysis includes mechanical, physical or chemical approaches. The purified nucleic acid is then used to genotype the above SNPs. The nucleic acid is added to a buffer, enzymes, specific primers and/or probes. This can be done in any suitable device such as tube, plate, well, glass etc. The genotype of the above SNPs may be detected by PCR, RFLP, allele-specific PCR, quantitative PCR, sequencing, microarray, hybridization, etc.

Sequencing can be performed using automatic sequencers using various techniques and following state of the art protocols. The sequencing reactions can be performed on complete genes or on specific regions covering the SNPs. For standard sequencing, the reaction requires a piece of DNA that initiates the amplification reaction, standard nucleotides and modified nucleotides that block the amplification reaction. Next generation sequencing can be performed by various techniques that massively amplified DNA regions.

Amplification can be performed using numerous techniques such as polymerase chain reaction (PCR), allele-specific PCR (ASA-PCR), PCR followed by a restriction enzyme digestion (RFLP-PCR) and quantitative PCR. These techniques are based on the amplification of specific regions using small pieces of DNA that hybridize to the specific regions and initiate the amplification reaction. The reaction also requires necessary components to make the amplification work such as nucleotides and enzymes. In the case of ASA-PCR, a multiplex reaction or independent reactions are used by mixing 4 pieces of DNA that will initiate the amplification reaction. Among these 4 pieces of DNA, 2 are specific to the SNP; one will be specific to the effect allele and the other will be specific to the non-effect allele. The sizes of the amplified regions would be different to be able to distinguish between them on a regular agarose gel. In the case of RFLP-PCR, the amplified material is treated using a restriction enzyme to cut the amplified region according to the SNP allele. For example, enzyme A would cut the effect allele, while it would not cut the non-effect allele. The sizes of the digested amplified region are distinguished on a regular agarose gel. For quantitative PCR, labelled probes specific to each allele are added to the amplification reaction to distinguish between the two alleles.

Genotyping can also be performed using hybridization techniques on a solid support or in suspension. These techniques are based on the hybridization of material amplified with allele specific probes and primers onto a support. The amplified material is labelled to distinguish the different alleles.

In the present invention, the prognostic method comprises the step of combining the genotyping data of step a) and the clinical risk factors of step b) on a decision support algorithm that gives a risk score, said risk score is calculated by the steps of:

(i) Allocating in step a) a value of 2 for subjects that are homozygous for the effect allele, a value of 1 for subjects that are heterozygous for both alleles and a value of o for subjects that are homozygous for the non-effect allele in the SNPs of rs1799853 (SEQ ID NO:1), rs4379368 (SEQ ID NO:2), rs6025 (SEQ ID NO:3), rs1 799963 (SEQ ID NO:4), rs8176719 (SEQ ID NO:5), rs8176750 (SEQ ID NO:6), rs9574 (SEQ ID NO:7), rs2289252 (SEQ ID NO:8), and rs710446 (SEQ ID NO:9);

(ii) Allocating in step b) a correlating value for the smoking status, the BMI, the age, the familial history of blood clotting diseases:

(iii) Calculating the Pill Protect® score (PP)

(iv) Calculating the absolute risk of the patient (AR)

(v) Analysing the PP and AR risk scores to determine the risk of the patient to develop a blood clotting disease.

The highest naturally occurring risk of thrombosis for woman is during the period of post-partum. As the risk of thrombosis always exists even without any hormonal change, the risk calculated by the prognostic method of the invention is compared with the risk of woman during the post-partum period.

A score PP>20 is indicative that said woman subject has a risk as high as the natural risk during postpartum period of having or developing a blood clotting disease.

The score Pill Protect® (PP) is calculated as follows:

$$PP = \exp(Po + P1x1 + \ldots + Pnxn)/\exp(Po + P1x1s1 + \ldots + PnXnst)$$

wherein:
Po=coefficient linked to the risk to develop the disease not related to the variables 1 to n.
P1=regression coefficient that correlates with the risk to develop thrombosis associated with the variable 1. The coefficient can be from $-\infty$ to $+\infty$.
x1=value taken by the variable 1. The range of possible values depends on the variable.
pn=regression coefficient that correlates with the risk to develop thrombosis associated with the variable n, the coefficient can be from $-\infty$ to $+\infty$.
Xn=value taken by the variable n. The range of possible values depends on the variable.
XJst=value taken by the variable 1 for a standard woman. The value depends on the variable.
Xnst=value taken by the variable n for a standard woman. The value depends on the variable.

The standard woman corresponds to a woman with a BMI of 23, age 20, she does not smoke, has no familial history of thrombosis and has the most frequent allele for each SNP (the most frequent allele corresponds to the non-effect allele for all SNPs except for rs9574 which is the effect allele (G;G)).

In particular, the genotyping data of step (i) include three possibilities which are homozygous for the "effect-allele", heterozygous or homozygous for the "allele with no effect".

Table 3 gives the detailed genotypes for each SNP (A: Adenine, G: Guanine, C: Cytosine, T: Thymine, -: deletion).

The BMI and age are used as continuous variables. Smoking status and familial history are binary variables.

TABLE 3

| | Genotype | | |
|---|---|---|---|
| SNP | Homozygous for the "effect allele" | Heterozygous | Homozygous for the "non-effect allele" |
| rs1799853 | (T; T) | (C; T) | (C; C) |
| rs4379368 | (T; T) | (C; T) | (C; C) |
| rs6025 | (A; A) | (A; G) | (G; G) |
| rs1799963 | (A; A) | (A; G) | (G; G) |
| rs8176719 | (G; G) | (-; G) | (-; -) |
| rs8176750 | (-; -) | (-; C) | (C; C) |
| rs9574 | (G; G) | (C; G) | (C; C) |
| rs2289252 | (T; T) | (C; T) | (C; C) |
| rs710446 | (G; G) | (A; G) | (A; A) |
| value of variable $x_n$ | 2 | 1 | 0 |

As used herein, the term "effect allele" refers to the allele that confers the risk to develop thromboembolic disease and/or the protective effect to develop a blood clotting disease to a woman subject undergoing a change in hormone levels.

As used herein, the term "non-effect allele" refers to the allele that does not confer a risk or a protective effect to develop a blood clotting disease to a woman subject undergoing a change in hormone levels.

In particular, the type of hormone present in the subject's treatment is also taken into account as a variable x. It includes the progestins: levonorgestrel, norgestimate, gestoden, desogestrel, drospirenone, dienogest, cyproterone acetate, in particular but not exclusively and also the estrogens estradiol, ethinylestradiol, estradiol acetate, estradiol cypionate, estradiol valerate, estradiol enanthate, estradiol benzoate, estradiol hemihydrate, in particular but not exclusively. It also includes progestin-only pills, intrauterine devices and hormone replacement therapy according to the route of administration such as oral or transdermal patch and other therapy such as Livial (Tibolone).

The absolute risk takes into account the incidence of blood clotting development according to the age range. The absolute risk (AR) is calculated as follows:

$$AR = adjPP * \text{the incidence according to the subject's age}$$

wherein:
adjPP is calculated as for PP but the age variable for the standard woman would be adjusted for the same age as the patient.
"the incidence according to the subject's age" is correlated to 0.5 for a subject of 15-20 years old, 2.5 for a subject of 20-30 years old, 3.5 for a subject of 30-40 years old, 5.5 for a subject of 40-50 years old, 10 for a subject of 50-60 years old, 50 for a subject of 60-75 years old, 100 for a subject of >75 years old (table 5);

As used herein, the "incidence" according to the subject's age has been determined based on the existing literature (Lidegraad 0, BMJ, 2011. Oger E, Thromb Haemost, 2000, Silverstein R L. Blood 2007). Table 4 lists the used incidence for 10'000 women per year.

TABLE 4

| Age | Incidence value |
| --- | --- |
| 15-20 y.o. | 0.5 |
| 20-30 y.o. | 2.5 |
| 30-40 y.o. | 3.5 |
| 40-50 y.o. | 5.5 |
| 50-60 y.o. | 10 |
| 60-75 y.o. | 50 |
| >75 y.o. | 100 |

The invention also provides an apparatus for calculating an estimation value of the risk of developing a blood clotting disease in a woman subject undergoing a change in hormone levels based on the woman subject-specific input features, said apparatus comprising:
a) a data interface for receiving said input features;
b) a processor for calculating said estimation value by applying a decision support algorithm as a function of numerical values derived from said received input features; and
c) a user interface for outputting said estimation value;
wherein said input features include a combination of:
  (i) the genotype of single nucleotide polymorphism of rs1799853 (SEQ ID NO:1), rs4379368 (SEQ ID NO:2), rs6025 (SEQ ID NO:3), rs1 799963 (SEQ ID NO:4), rs8176719 (SEQ ID NO:5), rs8176750 (SEQ ID NO:6), rs9574 (SEQ ID NO:7), rs2289252 (SEQ ID NO:8), and rs710446 (SEQ ID NO:9); and
  (ii) the clinical risk factors comprising the smoking status, the BMI, the age, the familial history of blood clotting diseases and the change in hormone levels of said woman subject.

Also provided is a method for calculating an estimation value of the risk of developing a blood clotting disease in a woman subject undergoing a change in hormone levels based on woman subject-specific input features, said method comprising:
a) selecting said input features to include a combination of:
  (i) the genotype of single nucleotide polymorphism of rs1 799853 (SEQ ID NO:1), rs4379368 (SEQ ID NO:2), rs6025 (SEQ ID NO:3), rs1 799963 (SEQ ID NO:4), rs8176719 (SEQ ID NO:5), rs8176750 (SEQ ID NO:6), rs9574 (SEQ ID NO:7), rs2289252 (SEQ ID NO:8), and rs710446 (SEQ ID NO:9); and
  (ii) the clinical risk factors comprising the smoking status, the BMI, the age, the familial history of blood clotting diseases and the change in hormone levels of said woman patient; and
b) calculating said estimation value by applying a decision support algorithm as a function of numerical values derived from said received input features.

Preferably, said method further comprises optimizing said input features by a learning process based on a stored dataset of a plurality of woman subjects to minimize a prediction error.

As shown in the example, the estimation of the risk of developing a blood clotting disease in a woman subject undergoing a change in hormone levels is very significant (example 1, FIG. 1 and example 2. FIG. 3) and the performance of the method was improved compared to conventional methods (example 1, FIG. 2 and example 2, Table 8).

The invention further provides a kit for use in identifying if a woman subject undergoing a change in hormone levels is having a risk of developing a blood clotting disease, said kit comprising:
i) at least one detection reagent for detecting the genotype of single nucleotide polymorphism of rs1 799853 (SEQ ID NO:1), rs4379368 (SEQ ID NO:2), rs6025 (SEQ ID NO:3), rs1 799963 (SEQ ID NO:4), rs8176719 (SEQ ID NO:5), rs8176750 (SEQ ID NO:6), rs9574 (SEQ ID NO:7), rs2289252 (SEQ ID NO:8), and rs710446 (SEQ ID NO:9);
and optionally
ii) instructions for use.

The kit contain necessary components to genotype the SNPs selected from the group comprising rs6025, rs1799963, rs8176719, rs8176750, rs9574, rs2289252, rs710446, rs4379368 and rs1 799853. These components include primers and/or probes specific to each SNP. The primers are necessary to initiate the amplification of each specific region corresponding to each SNP. The probes hybridize specifically to each allele of each SNP and allow the detection of each allele. The probes for each allele can be labelled with different fluorophores to allow distinct detection. The kit can also contain solid support to hybridize amplified material and allow the detection of each allele on the solid support after labelling reaction. The kit can also covers necessary reagents to sequence the regions around the 9 SNPs listed above or the full corresponding genes. These reagents include specific primers for each primer that would allow to initiate the amplification reaction and modified nucleotides.

Preferably, the SNP detection reagent is an isolated or synthetic DNA oligonucleotide probe or primer, or a RNA oligonucleotide or primer or a PNA oligomer or a combination thereof, that hybridizes to a fragment of a target nucleic acid molecule containing one of the SNPs specified in any one of SEQ ID Nos. 1 to 9, or a complement thereof.

In particular, said SNP detection reagent can differentiate between nucleic acids having a particular nucleotide at a target SNP position.

In the present invention, the SNP detection reagent hybridizes under stringent conditions to at least 8, 10, 12, 16, 18, 20, 22, 25, 30, 40, 50, 55, 60, 65, 70, 80, 90, 100, 120 or more consecutive nucleotides in a target nucleic acid molecule comprising at least one of the SNPs specified in any one of SEQ ID Nos. 1 to 9, or a complement thereof.

Preferably, according to the invention, at least one SNP detection reagent in the kit is an oligonucleotide or primer having a length of at least 8 nucleotides, preferably a length of at least 10, 12, 16, 17, 18, 19, 20, 21, 22, 23, 24 or 25 nucleotides.

The invention also relates to a kit for use, wherein the SNP detection reagent is a compound that is labelled.

In another separate embodiment, the present invention relates to a prognostic method for identifying if a woman subject undergoing a change in hormone levels is having a risk of developing a blood clotting disease, the method comprising:
  a) Obtaining a biological sample from a woman subject undergoing a change in hormone levels;
  b) Determining from said sample the genotype of single nucleotide polymorphisms rs1 799853 (SEQ ID NO:1), rs4379368 (SEQ ID NO:2), rs6025 (SEQ ID NO:3), rs1799963 (SEQ ID NO:4), rs8176719 (SEQ ID NO:5), rs8176750 (SEQ ID NO:6), rs9574 (SEQ ID NO:7), rs2289252 (SEQ ID NO:8), and rs710446 (SEQ ID NO:9);
  c) Determining the clinical risk factors of said woman subject, said clinical risk factors are selected from the group comprising the smoking status, the BMI, the age, the familial history of blood clotting diseases and the change in hormone levels;
  d) Combining the genotyping data of step b) and the clinical risk factors of step c) on a decision support algorithm that gives a risk score; and
  e) Analysing the risk score in order to determine the risk of said woman subject to develop a blood clotting disease; and
  f) Administering an effective amount of a compound adapted to the prevention of a blood clotting disease to said subject when the risk of developing a blood clotting disease is confirmed.

Compounds adapted to the prevention of a blood clotting disease are selected from the group comprising Apixaban, Rivaroxaban, Dabigatran, Edoxaban, heparin, vitamin K antagonists and coumarin drugs such as Warfarin.

The present invention relates also to a method of treatment of a woman subject undergoing a change in hormone levels having a risk of developing a blood clotting disease, the method comprising:
  a) Obtaining a biological sample from a woman subject undergoing a change in hormone levels;
  b) Determining from said sample the genotype of single nucleotide polymorphisms rs1799853 (SEQ ID NO: 1), rs4379368 (SEQ ID NO:2), rs6025 (SEQ ID NO:3), rs1799963 (SEQ ID NO:4), rs8176719 (SEQ ID NO:5), rs8176750 (SEQ ID NO:6), rs9574 (SEQ ID NO:7), rs2289252 (SEQ ID NO:8), and rs710446 (SEQ ID NO:9):
  c) Determining the clinical risk factors of said woman subject, said clinical risk factors are selected from the group comprising the smoking status, the BMI, the age, the familial history of blood clotting diseases and the change in hormone levels;
  d) Combining the genotyping data of step b) and the clinical risk factors of step c) on a decision support algorithm that gives a risk score;
  e) Analysing the risk score in order to determine the risk of said woman subject to develop a blood clotting disease; and
  f) Administering an effective amount of a compound adapted to the treatment of a blood clotting disease to said subject when the risk of developing a blood clotting disease is confirmed.

Compounds adapted to the treatment of a blood clotting disease are selected from the group comprising Apixaban, Rivaroxaban, Dabigatran, Edoxaban, heparin, vitamin K antagonists and coumarin drugs such as Warfarin.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended claims, and all changes which come within the meaning and range of equivalency are intended to be embraced therein.

Various references are cited throughout this specification, each of which 1s incorporated herein by reference in its entirety.

The foregoing description will be more fully understood with reference to the following Examples. Such examples are however exemplary of methods of practicing the present invention and are not intended to limit the scope of the invention.

EXAMPLE

Example 1: Performance of the Prognostic Method

Characteristics of the Studied Population

This study involved human subjects and was carried out in accordance with the tenets of the Declaration of Helsinki; all participants signed an informed consent. The study includes 794 female cases who have developed at least one episode of VTB while taking CC. These cases are part of the previously described PILI Genetic Risk Monitoring (PILGRIM) study (Suchan P, et al. (2017) Clin Genet: 91(1): 131-36), which relates the method used to confirm the occurrence of thrombosis. 828 control women were also collected from different sources: 523 are part of the PILGRIM study; 174 are part of the CoLaus study (Firmann M. et al. (2008) BMC Cardiovasc Disord:8:6). 56 were recruited between 1997 and 1998 in south of France and the remaining controls were recruited between 2012 and 2016 among Swiss population. These control women are taking CC but have not developed VTB by the time of the genotyping investigation.

Among 1622 women taking an oral contraceptive pill, 794 have developed a thrombotic event, either a deep vein thrombosis (DVT) or a pulmonary embolism (PE). Distribution of age, BMI and smoking status are presented in both populations (Tables 5 and 6). Age distribution is similar in both groups; BMI and smoking status are slightly higher in cases.

TABLE 5

| Clinical characteristics (mean) | Subjects (n = 794) | Controls (n = 828) |
|---|---|---|
| Age (years) | 32.3 | 31.5 |
| Body Mass Index (kg/m2) | 24 | 22.3 |
| Smoking status | 260 | 206 |

TABLE 6

|  | Cases (n) | Controls (n) |
|---|---|---|
| Total number | 794 | 828 |
| VTE | 794 |  |
| DVT | 600 |  |
| PE | 194 |  |
| Age (mean) | 32 | 31.5 |
| BMI (mean) | 24 | 23 |
| Family history of VTE | 222 | 19 |
| Smoking | 260 | 206 |

Genetic Determinants of Thrombotic Events (DVT+PE)

50 genetic polymorphisms were identified for all 1622 women in the study using Illumina's Veracode-BeadXpress technology. The selection of these SNPs was made according to the meta-analyses of the existing literature and the smaller-scale laboratory studies that we carried. In more details, SNPs were genotyped using Illumina GoldenGate technology and assessed using Illumina BeadXpress and GenomeStudio V2011.1 software. Clusters for each SNP were curated manually and undetermined samples were further genotyped using Sanger sequencing. SNP rs1053878 was genotyped using RFLP-PCR; in more details, the DNA region was amplified with the following primers (Forward: 5'-GCCACCGTGTCCACTACTATG-3' (SEQ ID NO: 10) and Reverse: 5'-GTCCACGCACACCAGGTAAT-3' (SEQ ID NO: 11)) and the amplicons were digested with PvuII restriction enzyme. Controls from the CoLaus cohort were previously genotyped as described (Kutalik Z, et al. (2011) Biostatistics; 12(1):1-17). For the CoLaus controls, proxys (r2>85%) were used for 9 SNPs (rs4572916 for rs10029715, rs8176704 for rs1053878, rs3736455 for rs13146272, rs6018 for rs1800595, rs4253417 for rs2289252, rs11038993 for rs3136516, rs2169682 for rs7082872, rs687621 for rs8176719 and rs2069952 for rs9574).

The following steps were performed on the cohort
(i) The cohort was randomly divided into a training set and a test set (out-of-sample approach).
(ii) a stepwise selection (AIC, Akaike information criterion) and a logistic regression using all variables (genetic and clinical variables) was performed to select variables and assign coefficients for each clinical variable and each SNP.
(iii) The fitted model was applied to the test set to compute predictions.
(iv) The predictions and thrombosis state of the women in the test set were stored.

This process was repeated 10'000 times ("runs"). Each run selected a number of variables as significant. When the variable was not selected, the coefficient was set to 0. Then the median of the coefficients for each variable over the 10'000 runs was calculated. All variables that had a non-zero median were selected in the final model.

Logistic regression models were fitted step-wise to find the optimal multivariate model in the 10,000 training sets. By averaging these 10,000 models, 4 clinical variables were identified as risk factors contributing to the prediction of the risk of VTB in our population. Age, BMI, smoking status and family history were selected and had significant p-values (Table 7), 9 out of the 46 tested SNP % were in the averaged model and also significantly associated with the development of thrombosis (Table 7).

This approach selected 9 SNPs and 4 clinical factors (Table 7). The p-value and Odd-Ratio (OR) indicate the significance and the strength, respectively, of the association between a SNP and the development of thrombosis.

TABLE 7

| Factor | Gene | Change | p-value[1] | OR[2] |
|---|---|---|---|---|
| rs6025 (SEQ ID NO: 3) | Factor V gene (NG_011806) | G > A | $8.3 \times 10^{-14}$ | 6.46 |
| rs1799963 (SEQ ID NO: 4) | Factor II gene (NG_008953) | G > A | $3.7 \times 10^{-8}$ | 5.32 |
| rs8176719 (SEQ ID NO: 5) | ABO gene (NG_006669) | - > G | $6.0 \times 10^{-7}$ | 1.52 |
| rs8176750 (SEQ ID NO: 6) | ABO gene (NG_006669) | C > - | $2.5 \times 10^{-3}$ | 0.59 |
| rs9574 (SEQ ID NO: 7) | PROCR gene (NG_032899) | C > G | $9 \times 10^{-4}$ | 1.25 |
| rs2289252 (SEQ ID NO: 8) | Factor 11 gene (NG_008051) | C > T | $2.9 \times 10^{-4}$ | 1.34 |
| rs710446 (SEQ ID NO: 9) | KNG1 gene (NG_016009) | A > G | $3.8 \times 10^{-2}$ | 1.22 |

TABLE 7-continued

| Factor | Gene | Change | p-value[1] | OR[2] |
|---|---|---|---|---|
| rs1799853 (SEQ ID NO: 1) | CYP2C9 gene (NG_008385) | C > T | $5.0 \times 10^{-4}$ | 1.55 |
| rs4379368 (SEQ ID NO: 2) | SUGCT gene (NG_023422) | C > T | $3.6 \times 10^{-2}$ | 1.35 |
| age | | | $4 \times 10^{-2}$ | 1.01 |
| Smoking status | | | $1.5 \times 10^{-4}$ | 1.63 |
| BMI | | | $8.9 \times 10^{-7}$ | 1.07 |
| Familial history | | | $2.4 \times ^{-7}$ | 2.13 |

[1]p-values obtained from the cohort of 1622 women and a logistic regression on the whole population
[2]Odd-Ratio obtained from the cohort of 1622 women and a logistic regression in an out-of-sample approach The Odd-Ratio (OR) quantifies the association between two parameters in a given population (Cornfield J., (1951). Journal of the National Cancer Institute. 11: 1269-1275). These values are obtained from mathematical models such as the logistic regression used herein. A logistic regression is a mathematical model that measures the relationship between variables by predicting the probability of a given outcome (Walker. S. H.; Duncan, D. B. (1967). Biometrika. 54: 167-178). The OR and p-values are the output of the logistic regression and correspond to the strength and the significance of the measured relationship respectively. Different approaches can be used to generate the p-values. In table 6, the p-values have been determined from 10'000 repetitions of a logistic regression using the whole 1622 women population whilst other approaches generate p-values using a logistic regression only on half of the population randomly selected 10'000 times in an out-of-sample manner.

FIG. 1 represents the distribution of the scores Pill Protect® (PP) across the controls represented by subjects who did not developed DVT and/or PE (wo TEV) and the subjects that developed DVT and/or PE (with TEV). The distribution is shown as a boxplot, where the thick line in the box is the median (second quartile), the bottom of the box is the first quartile, the top of the box is the third quartile, the whiskers represent the last point before outliers. As shown on FIG. 1, the difference between the score distribution of the subjects and controls is statistically significant (p-value=10-$^3$). The scores of the controls range from 1.9 to 1891 with a mean of 22 and a median of 12 while the scores of the subjects range from 3.5 to 17'419 with a mean of 97 and a median of 24.

Efficiency and Specificity of the Test
The following algorithm:

$$PP = \exp(Po + P1x1 + \ldots + Pnxn)/\exp(Po + P1x1st + \ldots + PnXnst)$$

was then applied to the test set and the predictions were plotted using a ROC curve to measure the efficiency of the test (AUC=71%—algorithm PP). In comparison, similar algorithms using only the clinical variables with coefficients generated from the literature (AUC=61%—algorithm MD) or using the clinical variables and Factor V and Factor II with coefficients generated from the literature (AUC=65%—algorithm MDg), were also used and the predictions computed into a ROC curve. The MD algorithm is the most representative of the medical questionnaire currently used by physician to estimate the risk of DVT, whilst the MDg is the most representative of the medical questionnaire currently used plus genetic testing that are currently available (Factor V and Factor II only). The three ROC curves are shown in FIG. 2.

In FIG. 2, the top curve (full line) represents the most efficient test and corresponds to the algorithm PP. The two other ROC curves (straight dashed and dotted lines) correspond to estimated values generated by meta-analysis of the literature as follows:

MD=bmi*smo*famh;

bmi=2.31 when patient's BMI is 30 or 1.43 when patient's BMI is 25 smo=1 if the patient is non-smoker or 1.6 if the patient is smoker famh=1 if the patient has no familial history of thrombosis event or 2 if the patient has a familial history of thrombosis event.

MDg=bmi*smo*famh*FV*FII:

bmi, smo and famh as stated above

FV=rs6025=1 if the patient is wt for rs6025, 4.11 if the patient is heterozygous for rs6025 or 11.15 if the patient is homozygous for the effect allele of rs6025

FIi=rs1 799963=1 if the patient is wt for rs1 799963, 3.5 if the patient is heterozygous for rs1 799963 or 8.4 if the patient is homozygous for the effect allele of rs1799963

A ROC (Receiver Operating Characteristic) curve is established and measures how well the different models discriminate the women at risk from the women without risk. The true positive rate (TPR) is plotted against the false positive rate (FPR) at various threshold settings (Fawcett T., (2006), *Pattern Recognition Letters.*, 27: 861-874).

The Area Under the Curve (AUC) is the probability that a positive test ranks higher than a negative test in order to discriminate the women at risk to the women without risk. The AUC (Area Under the Curve) ranges from 0.5 (50%—no predictive value) to 1 (100%—perfect discrimination; Fawcett T., (2006), *Pattern Recognition Letters.*, 27: 861-874). There are several ways to calculate AUC, either using the whole 1622 women population or using only the test set that corresponds to half of the population that was not used to select variables. The AUC presented in the text above have been calculated using the whole 1622 women population.

These results demonstrate that the score Pill Protect® detects more women at risk than that of the current standard of practice with or without genetic testing.

Table 8 discloses the AUC of three different models. The genetic score described by De Haan et al. (de Haan H G, et al. (2012) Blood; 120(3):656-63) is based on 5 SNPs (rs6025, rs1 799963, rs8176719, rs2066865, rs2036914). 3 of these SNPs are in common with the final model. Applying this 5 SNPs model to the half of the population of 1622 women yielded an AUC of 0.64 (0.62-0.68), which is less than the described AUC on MEGA and LETS cohorts (0.69 and 0.67 respectively) due to winners curse.

The genetic score described by Bruzelius et al. (Bruzelius M, et al. (2015) J Thromb Haemost; 13(2):219-27) is based on 7 SNPs (rs6025, rs1 799963, rs514659, rs2289252, rs1 799810, rs710446, rs2066865) and 4 interactions. The genotyping data for one SNP is not known among these 7 SNPs (rs1799810) and it was, therefore, not used in the comparison. The genetic score associated with this set of six SNPs reaches an AUC of 0.65 (0.63-0.68) in the present study which is very similar to what was described by Bruzelius et al. (0.66; 10.64-0.681). Still both AUC values are significantly below the 0.68 AUC of the 9 SNPs Pill Protect® model. The AUC presented in table 8 have been calculated using half of the population.

TABLE 8

| Model | AUC | 95% CI |
|---|---|---|
| Pill Protect ® model | 0.71 | 0.69-0.74 |
| Bruzelius genetics | 0.65 | 0.63-0.68 |
| De Haan genetics | 0.64 | 0.62-0.68 |

CI: confidence interval

As represented by the ROC curves, the risk estimated from Pill Protect® model improves the performance to determine whether a woman is at risk of developing DVT or PE.

Example 2: Determination of the Risk for Women Under Hormonal Contraceptives

Table 9 discloses the genotype and clinical parameters of women under hormonal contraceptives. The genotype of SEQ ID NO:1 to SEQ ID NO:9 and various clinical parameters have been determined as follows:

For each patient, the family history, the BMI, the age, the smoking status, and the genotype of SEQ ID NO:1 to SEQ ID NO:9 has been indicated by values as follows:

Family history: 0=no family history of blood clotting disease, 1=family history (first grade) of blood clotting disease.

Smoking status: 0 corresponds to a non-smoking subject and 1 corresponds to a smoking subject.

Value of SEQ ID NO: I to SEQ ID NO:9 is 2=homozygous for the effect allele, 1=heterozygous for the effect allele, 0=homozygous for the non-effect allele.

The development of a deep vein thrombosis (DVT) or a pulmonary embolism (PE) is indicated for each patient.

TABLE 9

| | SEQ ID NO: | | | | | | | | | Clinical Parameters | | | |
| | | | | | | | | | | Family | | | |
| Patient | 1 | 2 | 3 | 4 | 5 | 6 | 7 | 8 | 9 | History | BMI | Age | Smoking |
|---|---|---|---|---|---|---|---|---|---|---|---|---|---|
| 1 | 1 | 0 | 0 | 1 | 1 | 0 | 1 | 2 | 2 | 1 | 22.79 | 34 | 1 |
| 2 | 1 | 1 | 1 | 0 | 1 | 0 | 1 | 2 | 2 | 0 | 20.45 | 15 | 0 |
| 3 | 1 | 1 | 1 | 0 | 1 | 0 | 0 | 0 | 2 | 0 | 20.42 | 21 | 1 |
| 4 | 1 | 0 | 1 | 0 | 1 | 0 | 0 | 1 | 2 | 0 | 27.92 | 48 | 0 |
| 5 | 0 | 1 | 1 | 0 | 2 | 0 | 1 | 1 | 1 | 0 | 23.05 | 24 | 1 |
| 6 | 1 | 0 | 0 | 1 | 2 | 0 | 0 | 1 | 2 | 0 | 20.31 | 38 | 0 |
| 7 | 0 | 0 | 1 | 0 | 1 | 0 | 0 | 2 | 2 | 0 | 21.3 | 19 | 0 |
| 8 | 2 | 0 | 1 | 0 | 1 | 0 | 1 | 1 | 1 | 0 | 20.83 | 29 | 0 |
| 9 | 0 | 1 | 1 | 0 | 1 | 0 | 0 | 1 | 1 | 0 | 28.93 | 22 | 1 |
| 10 | 1 | 1 | 1 | 0 | 1 | 0 | 0 | 1 | 1 | 0 | 18.87 | 19 | 1 |

TABLE 9-continued

| Patient | SEQ ID NO: | | | | | | | | | Clinical Parameters | | | |
| | 1 | 2 | 3 | 4 | 5 | 6 | 7 | 8 | 9 | Family History | BMI | Age | Smoking |
|---|---|---|---|---|---|---|---|---|---|---|---|---|---|
| 11 | 1 | 1 | 0 | 1 | 1 | 0 | 1 | 1 | 1 | 1 | 20.76 | 16 | 0 |
| 12 | 2 | 0 | 0 | 1 | 1 | 0 | 2 | 2 | 1 | 0 | 24.14 | 19 | 0 |
| 13 | 0 | 1 | 1 | 0 | 0 | 0 | 0 | 0 | 0 | 0 | 21.97 | 25 | 1 |
| 14 | 0 | 0 | 1 | 0 | 1 | 0 | 1 | 0 | 1 | 0 | 21.8 | 19 | 1 |
| 15 | 0 | 0 | 0 | 1 | 1 | 1 | 1 | 0 | 0 | 0 | 22.955 | 42 | 0 |
| 16 | 0 | 0 | 0 | 1 | 1 | 0 | 1 | 1 | 0 | 0 | 22.463 | 42 | 0 |
| 17 | 0 | 0 | 0 | 0 | 0 | 0 | 1 | 2 | 0 | 1 | 16.9 | 29 | 1 |
| 18 | 0 | 1 | 0 | 0 | 0 | 0 | 1 | 0 | 0 | 1 | 19.72 | 20 | 0 |
| 19 | 0 | 0 | 0 | 0 | 0 | 0 | 1 | 1 | 0 | 1 | 18.37 | 27 | 1 |
| 20 | 0 | 0 | 0 | 0 | 1 | 0 | 1 | 0 | 0 | 1 | 19.53 | 20 | 0 |
| 21 | 0 | 0 | 0 | 0 | 0 | 0 | 0 | 0 | 1 | 1 | 20.4 | 23 | 1 |

For each patient, the following scores were calculated and reported in table 10.

Pill Protect® score (PP) calculated according to the formula described in the present invention taking into account genotyping data and clinical risk factors:

$$PP = \exp(Po + P1x1 + \ldots + Pnxn)/\exp(Po + P1x1st + \ldots + PnXnst)$$

Absolute risk (AR) calculated according to the formula described in the present invention taking into account the incidence of the disease:

$$AR = adjPP * \text{the incidence according to the subject's age}$$

DH score is a genetic score calculated as described in De Haan et al. based on rs6025, 10 rs1 799963, rs8176719, rs2066865, and rs2036914.

MD score is the current standard of practice without genetic testing and is calculated as described in the present invention:

$$MD = bmi * smo * famh:$$

bmi=2.31 when patient's BMI is 30 or 1.43 when patient's BMI is 25
smo=1 if the patient is non-smoker or 1.6 if the patient is smoker
famh=1 if the patient has no familial history of thrombosis event or 2 if the patient has a familial history of thrombosis event.

MDg score is the current standard of practice with genetic testing and is calculated as described in the present invention:

$$MDg = bmi * smo * famh * FV * FII:$$

bmi, smo and famh as stated above
FV=rs6025=1 if the patient is wt for rs6025, 4.11 if the patient is heterozygous for rs6025 or 11.15 if the patient is homozygous for the effect allele of rs6025
FIi=rs1 799963=1 if the patient is wt for rs1 799963, 3.5 if the patient is heterozygous for rs1 799963 or 8.4 if the patient is homozygous for the effect allele of rs1799963.

TABLE 10

| | Score | | | | | |
|---|---|---|---|---|---|---|
| Patient | PP | AR | DH | MD | MDg | DVT/PE |
| 1 | 107.88 | 306 | 5.14 | 2.00 | 7.00 | PE |
| 2 | 34.25 | 43 | 7.01 | 1.00 | 4.11 | DVT |
| 3 | 42.09 | 82 | 19.06 | 1.00 | 4.11 | DVT |
| 4 | 59.12 | 267.2 | 10.94 | 2.29 | 9.40 | DVT |
| 5 | 45.21 | 102 | 17.12 | 1.00 | 4.11 | DVT |
| 6 | 39.85 | 129 | 14.84 | 1.00 | 3.50 | DVT |
| 7 | 23.02 | 40 | 7.01 | 1.00 | 4.11 | PE |
| 8 | 29.48 | 76 | 7.01 | 1.00 | 4.11 | DVT |
| 9 | 52.90 | 108 | 10.94 | 1.43 | 5.88 | PE |
| 10 | 40.77 | 70 | 9.26 | 1.00 | 4.11 | DVT |
| 11 | 38.26 | 52 | 6.79 | 2.00 | 7.00 | PE |
| 12 | 28.19 | 49 | 5.14 | 1.00 | 3.50 | DVT |
| 13 | 14.15 | 33 | 5.00 | 1 | 4.11 | none |
| 14 | 14.22 | 24 | 9.26 | 1 | 4.11 | none |
| 15 | 5.12 | 19 | 5.14 | 1 | 3.5 | none |
| 16 | 11.13 | 41 | 6.79 | 1 | 3.5 | none |
| 17 | 3.75 | 10 | 1.00 | 2 | 2 | none |
| 18 | 1.86 | 3 | 1.56 | 2 | 2 | none |
| 19 | 3.01 | 7 | 2.06 | 2 | 2 | none |
| 20 | 2.08 | 4 | 3.22 | 2 | 2 | none |
| 21 | 3.71 | 8 | 1.74 | 2 | 2 | none |

In the present invention, a score PP>20 is indicative that a woman subject has a risk as high as the natural risk during postpartum period of having or developing a blood clotting disease. Table 10 shows that patients No. 1-12 with a Pill Protect® score PP>20 have developed a DVT or PE. Women with a Pill Protect® score PP<20 have not developed a DVT nor a PE so far. All of these women were taking an oral contraceptive. The current standard approach MD or MDg score does not discriminate women at risk from women not at risk as can be seen from similar results in patients No. 1-12 and patients No. 13-21. The DH score (DeHaan) does not discriminate neither the women at risk (low score (<20) for both cases and controls). On the other hand, the Pill Protect® score gives systematically a high score (PP>20) in all patients that have developed a DVT or PE compared to patients that have not developed a blood clotting disease.

Example 3: Determination of the Risk for Women Under Hormone Replacement Therapy Characteristics of the Studied Population Among 26 women above 45 years old and qualified to take hormone replacement therapy, 11 have developed a thrombotic event, either a deep vein thrombosis (DVT) or a pulmonary embolism (PE). Distribution of age. BMI and smoking status are presented in both populations (Table 11).

Age distribution is similar in both groups, BMI and Smoking status is slightly higher in subjects as expected, because they are known risk factors. However the BMI distribution is not so different that it will hide genetic factors.

TABLE 11

| Clinical characteristics (mean) | Subjects (n = 11) | Controls (n = 15) |
|---|---|---|
| Age (years) | 53.7 | 49.6 |
| Body Mass Index (kg/m2) | 25.5 | 22 |
| Smoking status | 3 | 2 |

FIG. 3 represents the distribution of the scores Pill Protect® (PP) across the controls subjects who did not develop DVT and/or PE (wo TEV) and the subjects that developed DVT and/or PE (with TEV) under or planning hormone replacement therapy. The distribution is shown as a boxplot, where the thick line in the box is the median (second quartile), the bottom of the box is the first quartile, the top of the box is the third quartile, the whiskers represent the last point before outliers.

The difference between the score distribution of the subjects and controls is dependent on the number of women (N=26, p-value=0.044). The scores of the controls range from 1.52 to 5.8 with a mean of 3.8 of and a median of 3.8 while the scores of the subjects range from 2.48 to 43 with a mean of 11.8 and a median of 7.3.

Performance of the Test

As shown in table 12, when compared to the current standard of care (the medical questionnaire), the following performances of the test were obtained:

TABLE 12

| Algorithm | PP score | MD score |
|---|---|---|
| True Positive women (TP) | 6 subjects | 3 subjects |
| False Positive women (FP) | 0 control | 1 control |
| True Negative women (TN) | 15 controls | 14 controls |

TABLE 12-continued

| Algorithm | PP score | MD score |
|---|---|---|
| False Negative women (FN) | 5 subjects | 8 subjects |
| PPV | 100% | 75% |
| NPV | 75% | 64% |
| specificity | 100% | 93% |
| sensitivity | 54% | 27% |

In table 12. "True Positive women" refers to the subjects that have developed a DVT and/or PE and have a PP score equal or above 7 or a MD score equal or above 3; "False Positive women" are the controls subjects that have not developed a DVT and/or PE and have a PP score equal or above 7 or a MD score equal or above 3; "True Negative women" are the controls subjects that have not developed a DVT and/or PE and have a PP score below 7 or a MD score below 3; and "False Negative women" are the subjects that have developed a DVT and/or PE and have a PP score below 7 or a MD score below 3.

The term "PPV" refers to "Positive Predicted Value". It represents the percentage of women with a positive test result who truly have developed the DVT and/or PE and is calculated by the formula PPV=TP/(TP+FP).

"NPV" refers to "Negative Predicted Value". It represents the percentage of women with a negative test result who did not develop the DVT and/or PE and is calculated by the formula TN/(TN+FN).

"Specificity" is calculated by the formula TN/(TN+FP) and the "Sensitivity" by the formula TP/(TP+FN).

A threshold of 7 was chosen for the PP algorithm. When taking into account the elevated incidence in women over 50 years old, which is 2 to 4 times higher than women between 20 and 50 years old, it corresponds to the highest natural risk of a woman's lifetime that is in postpartum (20).

A threshold of 3 was chosen for the MD algorithm because it corresponds to a combination of at least 2 of the 3 clinical variables.

The performance of the Pill Protect® (PP) test is higher than the current standard of care (MD score) for the PPV, NPV, specificity and sensitivity (Table 12).

The invention claimed is:

1. A treatment method for a woman subject undergoing a change in hormone levels having a risk of developing a blood clotting disease, the method comprising:
   determining, in a sample from said woman subject,
      genotyping data including the single nucleotide polymorphisms of rs1799853 (SEQ ID NO:1), rs4379368 (SEQ ID NO:2), rs6025 (SEQ ID NO:3), rs1799963 (SEQ ID NO:4), rs8176719 (SEQ ID NO:5), rs8176750 (SEQ ID NO:6), rs9574 (SEQ ID NO:7), rs2289252 (SEQ ID NO:8), and rs710446 (SEQ ID NO:9);
   computing a risk score of the woman subject for developing a blood clotting disease by combining (i) the genotyping data and (ii) clinical risk factors of the woman subject selected from the group consisting of smoking status, body mass index (BMI), age, familial history of blood clotting diseases, and change in hormone levels; and
   administering an effective amount of a compound adapted to the prevention of a blood clotting disease, to the woman subject on the basis of the computed risk score to decrease the risk of the woman subject for developing a blood clotting disease.

2. The treatment method according to claim 1, wherein said woman subject is undergoing the change in hormone levels due to having a contraceptive, having a combined contraceptive, having a hormonal replacement therapy, having a progestin-only contraceptive, being pregnant, having assisted reproductive technology, or being postpartum.

3. The treatment method according to claim 1, wherein:
   the woman subject has a risk of developing a blood clotting disease selected from the group consisting of deep vein thrombosis, pulmonary embolism, vein thrombosis and arterial thrombosis, and the familial history of blood clotting diseases includes a familial history of blood clotting diseases selected from the group consisting of deep vein thrombosis, pulmonary embolism, vein thrombosis and arterial thrombosis.

4. The treatment method according to claim 1, wherein the genotyping data is determined by nucleic acid sequencing and/or by PCR analysis.

5. A treatment method for a woman subject undergoing a change in hormone levels, said method comprising: selecting woman subject-specific input features comprising:
   (i) the genotype of single nucleotide polymorphisms of rs1799853 (SEQ ID NO:1), rs4379368 (SEQ ID NO:2), rs6025 (SEQ ID NO:3), rs1799963 (SEQ ID NO:4), rs8176719 (SEQ ID NO:5), rs8176750 (SEQ ID NO:6), rs9574 (SEQ ID NO:7), rs2289252 (SEQ ID NO:8), and rs710446 (SEQ ID NO:9); and
   (ii) the clinical risk factors of the woman subject comprising smoking status, BMI, age, familial history of blood clotting diseases and change in hormone levels of said woman subject;
   computing an estimation value by applying a decision support algorithm as a function of numerical values derived from the selected input features; and
   administering an effective amount of a compound adapted to the prevention of a blood clotting disease, to the woman subject on the basis of the computed estimation value to decrease the risk of the woman subject for developing a blood clotting disease.

6. The method according to claim 5, further comprising optimizing said input features by a learning process based on a stored dataset of a plurality of woman subjects so as to minimize a prediction error.

* * * * *

SEQUENCE LISTING

```
<160> NUMBER OF SEQ ID NOS: 11

<210> SEQ ID NO 1
<211> LENGTH: 51
<212> TYPE: DNA
<213> ORGANISM: Homo sapiens
<220> FEATURE:
<221> NAME/KEY: misc_feature
<223> OTHER INFORMATION: "n" is C or T
<220> FEATURE:
<221> NAME/KEY: misc_feature
<222> LOCATION: (26)..(26)
<223> OTHER INFORMATION: n is a, c, g, or t

<400> SEQUENCE: 1
gatggggaag aggagcattg aggacngtgt tcaagaggaa gcccgctgcc t          51

<210> SEQ ID NO 2
<211> LENGTH: 51
<212> TYPE: DNA
<213> ORGANISM: Homo sapiens
<220> FEATURE:
<221> NAME/KEY: misc_feature
```

<223> OTHER INFORMATION: "n" is C or T
<220> FEATURE:
<221> NAME/KEY: misc_feature
<222> LOCATION: (26)..(26)
<223> OTHER INFORMATION: n is a, c, g, or t

<400> SEQUENCE: 2
tggatggtat tgactttac atcacngaag gtgtttccat agatggaaga c        51

<210> SEQ ID NO 3
<211> LENGTH: 51
<212> TYPE: DNA
<213> ORGANISM: Homo sapiens
<220> FEATURE:
<221> NAME/KEY: misc_feature
<223> OTHER INFORMATION: "n" is A or G
<220> FEATURE:
<221> NAME/KEY: misc_feature
<222> LOCATION: (26)..(26)
<223> OTHER INFORMATION: n is a, c, g, or t

<400> SEQUENCE: 3
tgtaagagca gatccctgga caggcnagga atacaggtat tttgtccttg a        51

<210> SEQ ID NO 4
<211> LENGTH: 51
<212> TYPE: DNA
<213> ORGANISM: Homo sapiens
<220> FEATURE:
<221> NAME/KEY: misc_feature
<223> OTHER INFORMATION: "n" is A or G
<220> FEATURE:
<221> NAME/KEY: misc_feature
<222> LOCATION: (26)..(26)
<223> OTHER INFORMATION: n is a, c, g, or t

<400> SEQUENCE: 4
gttcccaata aaagtgactc tcagynagcc tcaatgctcc cagtgctatt c        51

<210> SEQ ID NO 5
<211> LENGTH: 51
<212> TYPE: DNA
<213> ORGANISM: Homo sapiens
<220> FEATURE:
<221> NAME/KEY: misc_feature
<223> OTHER INFORMATION: "n" is - or G
<220> FEATURE:
<221> NAME/KEY: misc_feature
<222> LOCATION: (26)..(26)
<223> OTHER INFORMATION: n is a, c, g, or t

<400> SEQUENCE: 5
gcagtaggaa ggatgtcctc gtggtnaccc cttggctggc tcccattgtc t        51

<210> SEQ ID NO 6
<211> LENGTH: 51
<212> TYPE: DNA
<213> ORGANISM: Homo sapiens
<220> FEATURE:
<221> NAME/KEY: misc_feature
<223> OTHER INFORMATION: "n" is - or C
<220> FEATURE:
<221> NAME/KEY: misc_feature
<222> LOCATION: (26)..(26)
<223> OTHER INFORMATION: n is a, c, g, or t

<400> SEQUENCE: 6
ccaagaacca ccaggcggtc cggaanccgt gagcggctgc caggggctct g        51

```
<210> SEQ ID NO 7
<211> LENGTH: 51
<212> TYPE: DNA
<213> ORGANISM: Homo sapiens
<220> FEATURE:
<221> NAME/KEY: misc_feature
<223> OTHER INFORMATION: "n" is C or G
<220> FEATURE:
<221> NAME/KEY: misc_feature
<222> LOCATION: (26)..(26)
<223> OTHER INFORMATION: n is a, c, g, or t

<400> SEQUENCE: 7
gcgatgttaa ttactctcca gccccntcag aaggggctgg attgatggag g        51

<210> SEQ ID NO 8
<211> LENGTH: 51
<212> TYPE: DNA
<213> ORGANISM: Homo sapiens
<220> FEATURE:
<221> NAME/KEY: misc_feature
<223> OTHER INFORMATION: "n" is C or T
<220> FEATURE:
<221> NAME/KEY: misc_feature
<222> LOCATION: (26)..(26)
<223> OTHER INFORMATION: n is a, c, g, or t

<400> SEQUENCE: 8
gtgagggtga ggcttgtctc tctctngccc tctcatcctg gcacatgtgc g        51

<210> SEQ ID NO 9
<211> LENGTH: 51
<212> TYPE: DNA
<213> ORGANISM: Homo sapiens
<220> FEATURE:
<221> NAME/KEY: misc_feature
<223> OTHER INFORMATION: "n" is A or G
<220> FEATURE:
<221> NAME/KEY: misc_feature
<222> LOCATION: (26)..(26)
<223> OTHER INFORMATION: n is a, c, g, or t

<400> SEQUENCE: 9
agggatccaa tcgtcatcac tctgtntggg agctggtgat ataggaggca t        51

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
gccaccgtgt ccactactat g                                         21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gtccacgcac accaggtaat                                           20
```